United States Patent [19]

Leone

[11] Patent Number: 5,674,198
[45] Date of Patent: Oct. 7, 1997

[54] TANDEM BALLOON CATHETER

[75] Inventor: James E. Leone, Miami, Fla.

[73] Assignee: Cordis Corporation, Miami Lakes, Fla.

[21] Appl. No.: 493,903

[22] Filed: Jun. 23, 1995

[51] Int. Cl.⁶ .................................................. A61M 25/00
[52] U.S. Cl. .................................................. 604/101; 604/49
[58] Field of Search .................... 604/96, 101, 49–54, 604/280, 102, 103, 104

[56] References Cited

U.S. PATENT DOCUMENTS

| | | |
|---|---|---|
| 4,423,725 | 1/1984 | Baran et al. . |
| 4,573,966 | 3/1986 | Weikl et al. . |
| 4,581,017 | 4/1986 | Sahota . |
| 4,610,662 | 9/1986 | Weikl et al. . |
| 4,824,436 | 4/1989 | Wolinsky . |
| 5,087,244 | 2/1992 | Wolinsky et al. . |
| 5,135,474 | 8/1992 | Swan et al. . |
| 5,135,484 | 8/1992 | Wright . |
| 5,195,955 | 3/1993 | Don Michael . |
| 5,222,941 | 6/1993 | Don Michael . |
| 5,328,470 | 7/1994 | Nabel et al. . |
| 5,415,636 | 5/1995 | Forman . |
| 5,462,529 | 10/1995 | Simpson et al. .......... 604/101 |

*Primary Examiner*—John D. Yasko
*Attorney, Agent, or Firm*—Gerstman, Ellis & McMillin, Ltd.

[57] ABSTRACT

A balloon catheter comprises a catheter shaft and a plurality of lumens, having a pair of spaced, inflatable balloons carried on the shaft to define an interballoon space between the balloons. Each of the balloons are connected to a separate inflation lumen to permit separate inflation and deflation. A fluid flow lumen extends through the catheter shaft and communicates with the interballoon space. Preferably, a perfusion lumen extends through the catheter shaft and the distal end to permit the shunting of blood past the inflated balloons. The spaced balloons are made of an elastomeric material, and are capable of being inflated to a diameter greater than their length. The catheter may be used by inflating a first catheter balloon to block a blood vessel. One then adds a therapeutic agent to the blood vessel at a position on one side of the first balloon through a flow lumen in the catheter. One then inflates a second catheter balloon to block the blood vessel and isolate the medication between the two balloons, while avoiding undue pressure increase in the interballoon space.

19 Claims, 1 Drawing Sheet

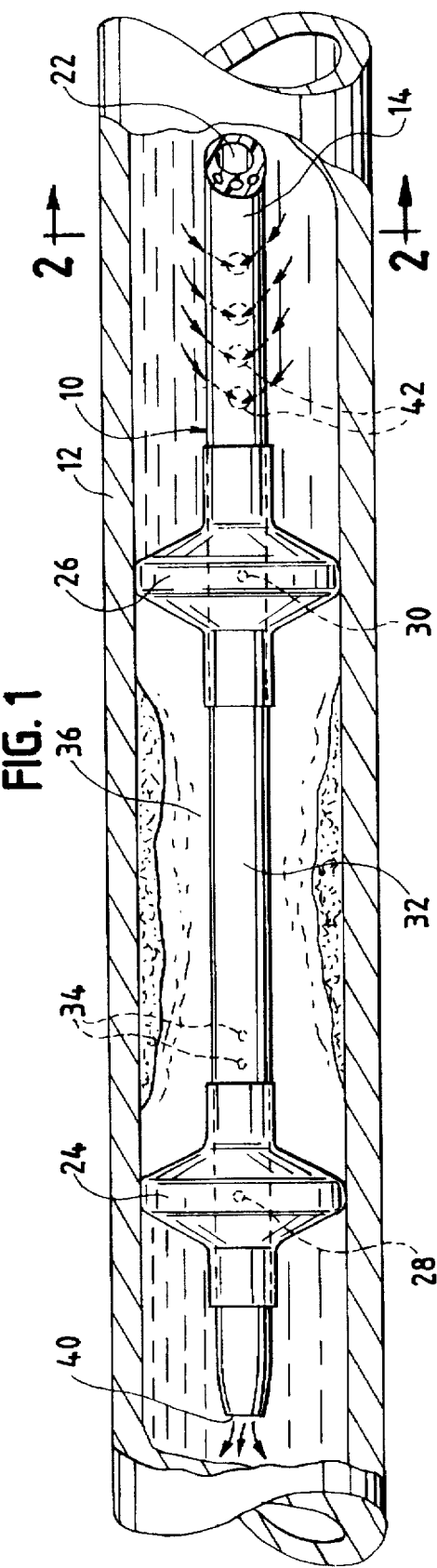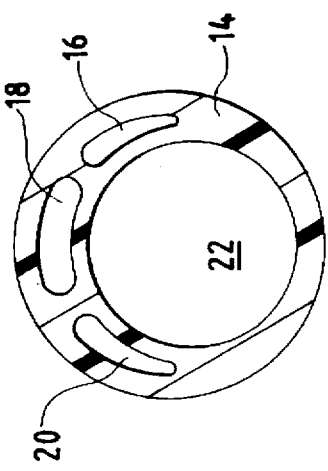

TANDEM BALLOON CATHETER

BACKGROUND OF THE INVENTION

Balloon catheters which have the capability of providing therapeutic solutions to a sealed area between balloons are known, for example in the following patents: Baran et al. U.S. Pat. No. 4,423,725; Wolinsky U.S. Pat. No. 4,824,436; Weikl et al. U.S. Pat. No. 4,610,662; Wright U.S. Pat. No. 5,135,484; and Michael U.S. Pat. No. 5,222,941. However, there is a need to provide therapeutic agents, such as agents for thrombin dissolution, to an isolated area in a human artery for the dissolving of stenotic materials and the like. For this purpose the catheters of the above-cited patents each exhibit significant disadvantages.

For example, when a pair of balloons are inflated in an artery to isolate an area for the application of a therapeutic agent such as heparin, a dissolution agent for thrombin, or any other appropriate medicament for treatment of arterial walls, the nature and quality of the balloons can have a significant effect on the success of the treatment. Similarly, the inflation of a spaced pair of balloons to isolate a portion of an artery causes the significant blockage of blood flow, which can lead to ischemia downstream in the artery. Thus in many prior art catheters the length of time that balloons may remain inflated is seriously curtailed. Often, a longer time is needed to obtain the best medical effect.

Also, after inflation of the balloons, the insertion of therapeutic agent into the isolated space between the balloons causes an undesirable increase in pressure, since the area is sealed by the balloons. This limits the amount of therapeutic agent that can be inserted in many of the prior art catheters. Also, retrieval of a therapeutic agent from the isolated space between the inflated balloons back into the catheter is difficult and incomplete with the use of the above double balloon catheters. This restricts the use of therapeutic agents which may have long term toxicity if left in the patient, but which in the short term may have significant medical advantage if they can be substantially removed at the end of the procedure.

The balloon catheter of this invention is capable of overcoming the prior art disadvantages listed above, while being relatively inexpensive and easy to use for desired medical treatments of the artery wall.

Additionally, the catheter of this invention can be used in any situation where it is desired to treat a limited area in the body which is closed off by the inflation of a pair of spaced balloons, for example for treatment with cancer chemotherapeutic agents, radioisotopes, and other materials including those having long term toxicity, which can be first inserted and then substantially completely withdrawn from a treatment area in the body.

DESCRIPTION OF THE INVENTION

By this invention a balloon catheter is provided which comprises a catheter shaft defining a plurality of lumens and having proximal and distal ends. A pair of spaced, inflatable balloons are carried on the catheter shaft to define an interballoon space between the balloons. Each of the balloons are optionally connected to a separate inflation lumen for separate inflation and deflation control of the respective balloons. A fluid flow lumen extends through the catheter shaft and communicates with the interballoon space, to provide therapeutic agents to the interballoon space, and also to permit the removal of the same therapeutic agents from the interballoon space.

In accordance with this invention, the spaced balloons may be made of an elastomeric material, contrary to the typical balloons currently used in angioplasty. Preferably, materials having an elongation to break of at least 100 percent may be used for the balloon. These balloons are preferably capable of being inflated to a diameter that is greater than their length. Thus, inflation of the balloons provides an annular seal which is suitable for sealing therapeutic agents within the interballoon space. At the same time, the relatively short length of the balloons causes them to press a smaller area of the arterial wall than is normal with conventional catheter balloons. This permits the balloons to remain inflated for a longer period of time than is customary without the onset of symptoms of ischemia in the tissue immediately adjacent to the inflated balloons. Also, the balloons seal with less fluid displacement.

Preferably, a perfusion lumen also extends through the catheter shaft and the distal end of the catheter, to provide a shunting path for blood to shunt through the balloons as they are inflated. Thus, blood can pass downstream through the balloons even though the balloons are inflated, providing the sealed-off interballoon space.

The balloons which are preferably used may be made of a polyurethane or similar plastic which has a more predictable pressure-diameter relation than polyolefin or natural rubber latex. In other words, by use of known polyurethane materials or the like, one can more accurately determine the maximum diameter of a catheter balloon just from the pressure being applied to it, than in the situation of polyolefin rubber latices, for example natural rubber latex. This provides the physician a way to control maximum balloon diameters during a medical procedure without direct observation of the balloon diameters.

The fluid flow lumen described above extends from the proximal end of the catheter through the catheter to a port which communicates with the interballoon space at a position that is preferably nearer to one of the spaced balloons than it is to the other of the spaced balloons. Typically, this position may be nearer to the distal balloon of the spaced, inflatable balloons, compared with the proximal balloon of such balloons. This facilitates the method of this invention, in which one inserts a catheter into a blood vessel of a patient, and inflates a first catheter balloon to block the blood vessel. One then adds a therapeutic agent to the blood vessel through a flow lumen in the catheter, which flow lumen is at a position on one side of the first catheter balloon. Then, after adding the agent, one inflates the second catheter balloon to block the blood vessel, thus creating the sealed, interballoon space with the medication substantially contained in the interballoon space. The second balloon is longitudinally spaced from the first balloon and on its one side to enclose the therapeutic agent between the balloons.

As a result of this, because the therapeutic agent is being added while one balloon is inflated and the other balloon is not, the interballoon space is substantially filled with a high concentration of such medication, the blood being in large measure pushed away by the medication. One then expands the second balloon to seal the area with the medication inside. Thus, even if the medication has toxicity, less of it will escape into the body in general.

Then, when the medicating process or other treatment is complete, one deflates one of the balloons, typically the balloon that is farther from the medication port in the catheter. One then can exert a suction to draw the therapeutic agent back through the medication port, with blood passing across the deflated balloon to replace the withdrawn medication. Then, the other balloon may be deflated and the catheter removed, leaving an area which has been treated with the desired medication, with most of the medication being removed again at the end of the treatment.

During this treatment, it is preferred to pass blood along a portion of the catheter to bypass the catheter balloons while the first and second balloons are inflated. This can be accomplished by means of the perfusion lumen described above.

Thus, a catheter and a method are provided in which the application of a therapeutic agent can be provided in a controlled manner, with the option of permitting the removal of most of the therapeutic agent at the end of the treatment. At the same time, the type of balloon used provides significant advantages to this particular process, in that the area of tissue pressed by the balloon periphery is relatively reduced, permitting longer applications of balloon inflation without the onset of local ischemia in the tissue. Also, the inflation of such balloons causes less displacement of blood or other fluid into the sealed chamber by their inflation because the balloon is preferably of a length that is less than its width, resulting in a volume reduction in the inflated balloon over typical, corresponding catheter balloons of the prior art. Thus, an unwanted pressure increase in the interballoon space can be avoided, when compared with conventional arterial catheter balloons which are longer than their inflated diameter.

Also, the use of a perfusion lumen can provide shunting of blood past the spaced balloons while the interballoon space remains isolated. Thus, treatment with a therapeutic agent can last for a longer period of time since ischemia of tissues downstream from the balloons can be reduced or avoided.

DESCRIPTION OF THE DRAWINGS

Referring to the drawings,

FIG. 1 is an elevational view, with portions broken away, of the distal end of a catheter in accordance with this invention, shown positioned in an artery to permit medical treatment of a portion of the artery;

FIG. 2 is an enlarged, longitudinal sectional view of the catheter of FIG. 1, taken along line 2—2 of FIG. 1; and FIG. 3 is a plan view of the proximal end of said catheter.

DESCRIPTION OF SPECIFIC EMBODIMENT

Referring to the drawings, the distal end of a double balloon therapeutic agent administration catheter 10 is shown emplaced in the artery 12 of a patient by a conventional technique. Catheter 10 may be of the conventional design of an angioplasty catheter except as otherwise indicated herein.

Catheter 10 defines a catheter shaft 14 which extends from a proximal branch connector 11 of conventional design having connector lines 15, 17, 19, 21 respectively in communication with each of the catheter lumens 16, 18, 20, 22 present, for the separate and independent flow of fluids through each of the lumens. Hub 23 connects members 15 and 16, 17 with 18, 19 with 20, and 21 with 22.

Catheter 10 also carries a pair of spaced balloons 24, 26. One of lumens 16–20 communicates with each of the respective balloons 24, 26 through an access port 28, 30 respectively formed in the catheter body. For example, lumen 16 may communicate with aperture 30 in the catheter wall, with lumen 16 terminating at that point. A distal segment 32 of the catheter wall then may lack lumen 16 but contain the other lumens, with lumen 20, for example, extending to wall aperture 28. Thus, a pair of inflation lumens 16, 20 are provided, if desired, for the independent inflation and separate inflation and deflation of balloons 24, 26.

The remaining small lumen of lumens 16–20, for example lumen 18, extends the length of the catheter and terminates in a pair of apertures 34 in catheter body portion 32, to communicate with the interballoon space 36 which comprises a sealed, annular area between the inflated balloons 24, 26 and the wall of artery 12.

In the embodiment shown, catheter 10 has been positioned so that balloons 24, 26 bracket an arterial stenosis 38 of the artery 10. Catheter 10 is of course inserted with balloons 24, 26 in their deflated condition. Then, after catheter 10 has been properly positioned, balloon 24 only may be inflated to the inflated condition shown. Because the width of balloon 24 is less than its expanded diameter, the advantages of this invention are achieved, with a relatively narrow seal which compresses less tissue area, and thus results in a slower onset of ischemia than is customary in prior art balloon inflations. Also the shorter balloons can provide a shorter interballoon space 36, typically of about 1 cm so that the space can be placed to avoid arterial side branches, and smaller amount of therapeutic agent can be used to fill the space 36, among other advantages.

Also, the respective balloons are made of an elastomeric material, contrary to the currently conventional angioplasty balloons, so that a good seal to the artery wall can be achieved at lower pressures, for even less ischemia of adjacent tissue. Such balloons may be made of a polyurethane formulation having a Shore A durometer of 40 to 90 and an elongation to break of 150 to 500 percent, for example. One usable polyurethane material is DuPont 80A polyurethane.

As previously stated, the physician can accurately estimate the maximum outer diameter of each balloon by the use of such a polyurethane which exhibits a more accurate pressure-diameter relation than, for example polybutadiene rubber latex. Thus, at a predetermined fluid pressure provided by the inflation lumens, the maximum diameters of the balloons may be accurately known.

Balloons 24, 26 may preferably inflate to a maximum diameter of 4 to 8 mm., and may have a length of 2–4 mm.

Thus, when balloon 24 is inflated, the physician then administers medicament from the proximal catheter end through lumen 18, so that the medicament or therapeutic solution exits the catheter interior through apertures 34 into the interballoon space. Because balloon 26 is deflated, the therapeutic solution may displace blood, which migrates across the deflated balloon 26 so that the interballoon space may become substantially filled with the therapeutic solument, for example, heparin or an enzyme for thrombin dissolution. Then, balloon 26 may also be inflated to provide a proximal end seal of the interballoon space 36, thus preventing much migration of the therapeutic agent out of interballoon space 36. The therapeutic agent remains in place for any desired length of time, for example to dissolve and remove the stenotic material 38.

Alternatively, both balloons may be inflated prior to inserting the therapeutic agent, to minimize any release of therapeutic agent into the body.

In this embodiment, the large, perfusion lumen 22 extends through the distal end 40 of catheter 10 at a location distal of balloons 24, 26. Perfusion lumen 22 also communicates with side apertures 42 at a position which is proximal to balloons 24, 26, to provide a shunt path for blood flow around or through the balloons. The shunt path extends into apertures 42, through lumen 22, and out into the artery again through open end 40 at the other side of the balloons. Thus, ischemia downstream of the inflated balloons can be suppressed while the therapeutic procedure is in process. Also, lumen 22 may serve as a guidewire lumen.

Then, at the end of the procedure, for of the balloons, for example balloon 26, can be again deflated as a suction is exerted on the proximal end of lumen 18, to cause the therapeutic solution, mixed with blood and pieces of stenotic material, to pass again through apertures 34 and then to proximally pass through the length of the catheter for removal. After a sufficient amount of the medicament or therapeutic solution has been removed, the other balloon 24, may also be deflated, and the catheter may be removed. Otherwise, the catheter may remain in place until the tissue downstream has been thoroughly oxygenated by blood flow, and the process may then be repeated.

Alternatively the interballoon space 36 may be completely drained of therapeutic solution and flushed through lumen (or lumens) 18 prior to depressurizing the two balloons 24, 26, when the therapeutic agent is particularly toxic.

Apertures 34 are preferably positioned adjacent to balloon 24 and remote from balloon 26, to facilitate more complete insertion and withdrawal of therapeutic solution from the interballoon space 36. Alternatively, apertures 34 could be adjacent to balloon 26 and remote from balloon 24.

Thus, therapeutic materials may be administered in relatively high concentrations that may have toxic effects if released to the whole body. For example, high concentrations of heparin may be applied, or proteolytic, amylase, or other types of enzymes may be administered in such very high concentrations. Antiplatelet, DNA, or antisense agents to prevent restenosis and the like, may also be used. They may then be substantially removed again through aperture 34 and lumen 18 so as to avoid toxic effects in the patient.

Thus, the administration of therapeutic solutions or medicaments may be provided in a controlled manner by this catheter, permitting effective, localized effect of the medicaments without side effects caused by the spread of high concentrations of the medicaments to other parts of the body.

The above has been offered for illustrative purposes only, and is not intended to limit the scope of the invention of this application, which is as defined in the claims below.

That which is claimed is:

1. A balloon catheter which comprises: a catheter shaft defining a plurality of lumens and proximal and distal catheter ends; a pair of spaced, inflatable balloons carried on said shaft to define an interballoon space between said balloons, each of said balloons being connected to a separate inflation lumen; a fluid flow lumen extending through said catheter shaft and communicating with the interballoon space to provide a therapeutic agent to the interballoon space, both of the spaced balloons being made of an elastomeric material having an elongation to break of at least 100 percent and capable of being inflated to a diameter that is greater than their length.

2. The catheter of claim 1 in which said fluid flow lumen communicates with the interballoon space at a position that is nearer to the distal balloon of said spaced, inflatable balloons than the proximal balloon of said balloons.

3. A balloon catheter which comprises: a catheter shaft defining a plurality of lumens and proximal and distal catheter ends; a pair of spaced, inflatable balloons carried on said shaft to define an interballoon space between said balloons, each of said balloons being connected to a separate inflation lumen; a fluid flow lumen extending through said catheter shaft and communicating with the interballoon space, the spaced balloons being made of an elastomeric material and capable of being inflated to a diameter that is greater than their length; said balloons being made of a polyurethane having a more accurate pressure-diameter relation than polyolefin rubber latex, said polyurethane having a Shore A durometer of 40 to 90 and an elongation to break of 150 to 500 percent.

4. The catheter of claim 1 in which said fluid flow lumen communicates with the interballoon space at a position that is adjacent to one of the spaced balloons and remote from the other spaced balloon.

5. A balloon catheter which comprises: a catheter shaft defining a plurality of lumens and proximal and distal catheter ends; a pair of spaced, inflatable balloons carried on said shaft to define an interballoon space between said balloons, each of said balloons being connected to a separate inflation lumen; a fluid flow lumen extending through said catheter shaft and communicating with the interballoon space, the spaced balloons being made of an elastomeric material and capable of being inflated to a diameter that is greater than their length; said fluid flow lumen communicates with the interballoon space at a position that is adjacent to one of the spaced balloons and remote from the other spaced balloon; said balloons being made of a polyurethane having a more accurate pressure-diameter relation than natural rubber latex.

6. The catheter of claim 1 further comprising a perfusion lumen extending through said catheter shaft and said distal end, to provide a shunting circuit for blood through said balloons while said balloons are inflated.

7. A balloon catheter which comprises: a catheter shaft defining a plurality of lumens and proximal and distal catheter ends; a pair of spaced, inflatable balloons carried on said shaft to define an interballoon space between said balloons, each of said balloons being connected to a separate inflation lumen; a fluid flow lumen extending through said catheter shaft and communicating with the interballoon space, the spaced balloons being made of an elastomeric material and capable of being inflated to a diameter that is greater than their length; a perfusion lumen extending through said catheter shaft and said distal end, to provide a shunting circuit for blood through said balloons while said balloons are inflated; said perfusion lumen being of larger cross sectional area than any of said inflation lumens and fluid flow lumen, said perfusion lumen being substantially circular in cross-sectional area while said inflation lumens and fluid flow lumen have a cross section comprising a wide dimension and a perpendicular narrow dimension, said wide dimension being less than the diameter of said perfusion lumen.

8. The catheter of claim 7 in which said fluid flow lumen communicates with the interballoon space at a position which is adjacent to one of said balloons and remote from the other of said balloons.

9. The catheter of claim 8 in which said balloons are made of a polyurethane having a more accurate pressure-diameter relation than polyolefin rubber latex.

10. The balloon catheter of claim 1 in which at least one of said spaced balloons has a length of 2 to 4 mm.

11. The balloon catheter of claim 1 in which at least one of said spaced balloons has a length of 2 to 4 mm.

12. The method of inserting a catheter into a blood vessel of a patient; inflating a first catheter balloon to block said blood vessel; adding a therapeutic agent to said blood vessel at a position on one side of said first catheter balloon through a flow lumen in said catheter; and then inflating a second catheter balloon to block said blood vessel, said second balloon being longitudinally spaced from said first balloon on said one side to enclose said therapeutic agent between said balloons, both of the spaced balloons being made of an elastomeric material having an elongation to break of at least 100 percent and capable of being inflated to a diameter that is greater than their length.

13. The method of inserting a catheter into a blood vessel of a patient; inflating a first catheter balloon to block said blood vessel; adding a therapeutic agent to said blood vessel at a position on one side of said first catheter balloon through a flow lumen in said catheter; and then inflating a second catheter balloon to block said blood vessel, said second balloon being longitudinally spaced from said first balloon on said one side to enclose said therapeutic agent between said balloons; and passing blood through a portion of said catheter to bypass said catheter balloons while said first and second balloons are inflated.

14. The method of claim 13 in which one thereafter deflates one of said balloons and withdraws at least some of said therapeutic agent from said blood vessel back into said catheter flow lumen, prior to deflating the other of said balloons.

15. The method of inserting a catheter into a blood vessel of a patient; inflating a first catheter balloon to block said blood vessel; adding a therapeutic agent to said blood vessel at a position on one side of said first catheter balloon through a flow lumen in said catheter; and then inflating a second catheter balloon to block said blood vessel, said second balloon being longitudinally spaced from said first balloon on said one side to enclose said therapeutic agent between said balloons; thereafter deflating one of said balloons and withdraws at least some of said therapeutic agent from said blood vessel back into said catheter flow lumen prior to deflating the other of said balloons.

16. A balloon catheter which comprises: a catheter shaft defining a plurality of lumens and proximal and distal catheter ends; a pair of spaced, inflatable balloons carried on said shaft to define an interballoon space between said balloons, each of said balloons being connected to an inflation lumen; a fluid flow lumen extending through said catheter shaft and communicating with the interballoon space, the spaced balloons being made of an elastomeric material and capable of being inflated to a diameter that is greater than their length, said catheter further comprising a perfusion lumen extending through said catheter shaft and said distal end, to provide a shunting path for blood through said balloons while said balloons are inflated, in which said perfusion lumen is of larger cross-sectional area than any of said inflation lumens and fluid flow lumen, said perfusion lumen being substantially circular in cross-section, said inflation lumens and fluid flow lumen having cross sections which have a large dimension and a substantially smaller perpendicular dimension, the large dimensions of said inflation lumens and fluid flow lumen being each less than the diameter of the cross section of said perfusion lumen.

17. The catheter of claim 16 in which said balloons are made of a polyurethane having a more accurate pressure-diameter relation than polyolefin rubber latex, said polyurethane having a Shore A durometer of 40 to 90 and an elongation to break of 150 to 500 percent.

18. The catheter of claim 16 in which said fluid flow lumen communicates with the interballoon space at a position that is adjacent to one of the spaced balloons and remote from the other spaced balloon.

19. The balloon catheter of claim 16 in which at least one of said spaced balloons has a length of 2 to 4 mm.

\* \* \* \* \*